US00PP12364P2

(12) United States Plant Patent
Utecht

(10) Patent No.: US PP12,364 P2
(45) Date of Patent: Jan. 22, 2002

(54) GERANIUM PLANT NAMED 'FISSIL'

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 09/631,665

(22) Filed: Aug. 3, 2000

(51) Int. Cl.[7] ..... A01H 5/00
(52) U.S. Cl. ..... Plt./329
(58) Field of Search ..... Plt./329, 325

(56) References Cited

PUBLICATIONS

Fischer Selections 1999/2000 Catalogue offering 'Brasil 99' ('Fissil') on p. 9.
Swiss Application for 'FISSIL' (Apr. 22, 1999).
European Union Application for 'FISSIL' (Aug. 17, 1998).
European Union Grant for 'FISSIL' (Aug. 16, 1999).
German Application for 'FISSIL' (Aug. 17, 1998).
German Grant for 'FISSIL' (Jan. 15, 1999).
Canadian Application, Denomination, Plant Varieties Journal No. 33, Oct. 1999 Canada.
GTITM UPOVROM Citation for 'Fissil' as per QZ PBR 980828; Jun. 15, 1998.*

* cited by examiner

*Primary Examiner*—Bruce R. Campell
*Assistant Examiner*—Kent L. Bell
(74) *Attorney, Agent, or Firm*—Foley & Lardner

(57) ABSTRACT

A new and distinct cultivar of geranium plant named 'Fissil', as described and illustrated, and particularly characterized by the combined features of brilliant purple colored single type flowers with red eyes, rich flowering with inflorescence borne well-above the foliage, uniformly dark-green foliage, medium-tall to tall, well-branched plant habit, and medium spring flowering response.

1 Drawing Sheet

BACKGROUND OF THE INVENTION

The present invention relates to a new and distinct cultivar of geranium plant, botanically known as *Pelargonium zonale,* and hereinafter referred to by the cultivar name 'Fissil'.

'Fissil' is a product of a planned breeding program which had the objective of creating new geranium varieties with purple-flower color and single-flower form in combination with dark-green foliage and fair, self-branching ability.

'Fissil' originated from a hybridization made by the inventor, Angelika Utecht, in a controlled breeding progam in Galdar, Gran Canaria, Spain, in 1994. The female parent was a seedling derived from a cross of a tetraploid line of the commercial variety 'Kardinal' (unpatented) and a hybrid seedling, designated no. 2198-2 (unpatented). The resulting seedling, designated no. 92-876-2 (unpatented), was characterized by purple, single-form flowers, dark-green, zoned foliage, late flowering response and poor branching. The male parent was a hybrid seedling, designated no. 94-1969-1 (unpatented), having semi-double, purple flowers with markings, dark-green leaves without zonation, and good branching characteristics.

'Fissil' was selected as one flowering plant within the progeny of the stated cross by the inventor, Angelika Utecht, in 1995 in a controlled environment in Galdar, Gran Canaria, Spain.

The first act of asexual reproduction of 'Fissil' was accomplished when vegetative cuttings were taken from the initial selection in the fall of 1995 in a controlled environment in Galdar, Gran Canaria, Spain, by, or under the supervision of, Angelika Utecht. Horticultural examination of plants grown from cuttings of the plant, initiated in May 1996 in Hillscheid, Germany, and continuing thereafter, has demonstrated that the combination of characteristics as herein disclosed for 'Fissil' are firmly fixed and are retained through successive generations of asexual reproduction.

BRIEF DESCRIPTION OF THE INVENTION

The following traits have been repeatedly observed and are determined to be basic characteristics of 'Fissil', which in combination distinguish this geranium as a new and distinct cultivar:

1. single-type, bright, purple-colored flowers with distinct red eyes/macules;

2. large umbels borne well-above the foliage;

3. uniformly dark-green foliage without zonation in mature leaves; young leaves may occasionally show slight zonation RHS 139 A;

4. medium to vigorous growth, and medium-tall, round plant habit;

5. medium (mid season) spring flowering response; and 6. relatively good branching characteristics for a dark-leafed variety.

'Fissil' has not been observed under all possible environmental conditions. The phenotype of the new cultivar may vary significantly with variations in environment such as temperature, light intensity and day length without any change in the genotype. The following observations, measurements, and comparisons describe plants grown in Hillscheid, Germany, and in Langley, British Columbia, Canada, under greenhouse conditions which approximate those generally used in commercial practice.

Of the many commercial cultivars known to the present inventor, the most similar in comparison to 'Fissil' are the commercial variety 'Fistangoli' (U.S. Plant patent application Ser. No. 09/323,110), and the parental variety 'Kardinal'. In comparison to 'Fistangoli', 'Fissil' has a similar main flower color, but its flowers are single-type and its petals show large red flares, which are not present on the flowers of 'Fistangoli'. Moreover, 'Fissil' grows distinctly more vigorously, branches more freely and is more floriferous than 'Fistangoli'.

In comparison to 'Kardinal', 'Fissil' has a different kind of marking on its petals and better branching ability. 'Kardinal' grows vigorously and has a tall, open plant habit, whereas 'Fissil' grows only moderately vigorously and develops plants that are bushy and evenly shaped and medium-sized or slightly taller.

BRIEF DESCRIPTION OF THE DRAWING

The accompanying photographic illustration shows typical flower and foliage characteristics of 'Fissil' with colors being as true as possible with an illustration of this type.

DETAILED BOTANICAL DESCRIPTION

The measurements were taken in Langley, British Columbia, Canada, on Jun. 15, 1999, 12 weeks after planting of rooted cuttings into 15-cm pots. The plants had not been pinched. In the following description, color references are made to The Royal Horticultural Society (R.H.S.) Colour Chart. The color values were determined indoors from plants developed in a greenhouse in May 1999 in Hillscheid, Germany.

Classification:

*Botanical.*—A hybrid of the species *Pelargonium zonale L'Hérit.*

*Commercial.*—Zonal geranium, cv. 'Fissil'.

Inflorescence:

*Type.*—Umbel.

*Shape.*—Semi-spherical.

*Average diameter.*—116 mm.

*Average depth.*—65 mm.

*Peduncle length.*—150 mm.

*Peduncle color.*—Green, RHS 137 D, often strong infusion of anthocyanin (reddish coloring RHS 181 A) on one side.

*Pedicel length.*—42 mm, with spur.

*Pedicel color.*—Base is green RHS 144 A; middle part varies from RHS 179 B to RHS 179 A, upper part is RHS 181 A.

*Number of flowers per umbel.*—About 25–30.

*Lastingness of umbel.*—Approxiamtely 18 days at 18° C.

*Corolla.*—Average diameter: 51 mm. Form: Single-type. Shape: Almost round, with the petals overlapping in parts, but with a slight gap between upper and lower petals. Number of petals: 5. Size of petals: Upper petals are 26–28 mm long, 18–19 mm wide; lower petals are 25–27 mm long, 24–25 mm wide. Shape of petals: Upper petals are spatulate to obovate, lower petals are obovate with attenuate base, upper end rounded, margin entire. Number of petaloids: None. Color (general tonality from a distance of 3 meters): Purple with red eyes. Color of upper petals: Between RHS 66 B and RHS 74 B. Color of lower petals: Between RHS 66 B and RHS 74 B. Markings of petals: Red flares, RHS 46 B, which are large on upper petals and somehwat smaller on lower petals; additionally, the base of the upper petals shows a more salmon tint, RHS 44 D, and reddish, branched veins, RHS 53 C. Color of lower surface of petals: Between RHS 67 B and RHS 74 B. Color of sepals: Outer surface is mainly green, RHS 143 A, red at the base RHS 181 A; inner surface is light green, RHS 143 A, base is RHS 179 B. Number of sepals: 5. Size of sepals: 11–12 mm long, 4 mm wide for the largest upper sepal, 2–3 mm wide for other sepals. Shape of sepals: Linear to lanceolate, acute tip, base truncate, surface weak with pubescence, margin entire.

*Bud (immediately before unfolding of the petals).*—Shape: Narrow elliptical. Color (sepals): Light-green, from RHS 143 A to RHS 143 B. Color (petals): Intense purple-red, RHS 66 A. Length: 14 mm. Width: 7 mm.

*Reproductive organs.*—Androecium: 7 fertile anthers, white filaments with reddish upper ends, and orange pollen RHS 33 A, large quantity of pollen produced. Gynoecium: 5–6-lobed stigma, purple, with pink filament, one pistil per flower. Fertility/seed set: Moderate seed set, mainly in late summer to autumn; oblong shaped seeds, 4–5 mm in length, brown RHS 177 B.

*Spring flowering response period.*—In Hillscheid, Germany, in 1999, plants had on average 0.4 flowers opened 9 weeks after planting of rooted cuttings.

*Outdoor flower production.*—Medium number of inflorescence, but relatively rich flowering in comparison to other varieties with purple flower color in combination with dark-green foliage; the flower count in 1999 in Hillscheid, Germany, indicated about 2.0 inflorescences per plant in mid-May.

*Durability.*—Comparatively little shattering for a single-flowered variety, realtively good rain resistance; flowers are not completely resistant to being scorched/burnt by the sun.

*Lastingness of individual bloom.*—Approimately 7–8 days at 18° C.

*Fragrance.*—None.

Plant:

*Foliage.*—Form: Kidney-shaped, with open to wide-open base. Margin: Bicrenated. Size of leaf: 83 mm wide, 50–55 mm long. Color of upper surface: Dark-green, about from RHS 137 A to RHS 137 B. Color of zonation: No zonation on mature leaves, very weak zonation, darker-green color RHS 139 A on young leaves. Petiole: 60–70 mm in length, 3 mm in diameter, about RHS 143C.

*General appearance and form.*—Internode length: 20–30 mm. Branching pattern: 6.9 branches. Plant size: 19.4 cm high as measured from the base of the stem/soil surface to the surface of the foliage canopy (without inflorescence), and 31.8 cm wide.

Disease/pest resistance/susceptibility: None observed to date.

I claim:

1. A new and distinct cultivar of geranium plant named 'Fissil', as described and illustrated.

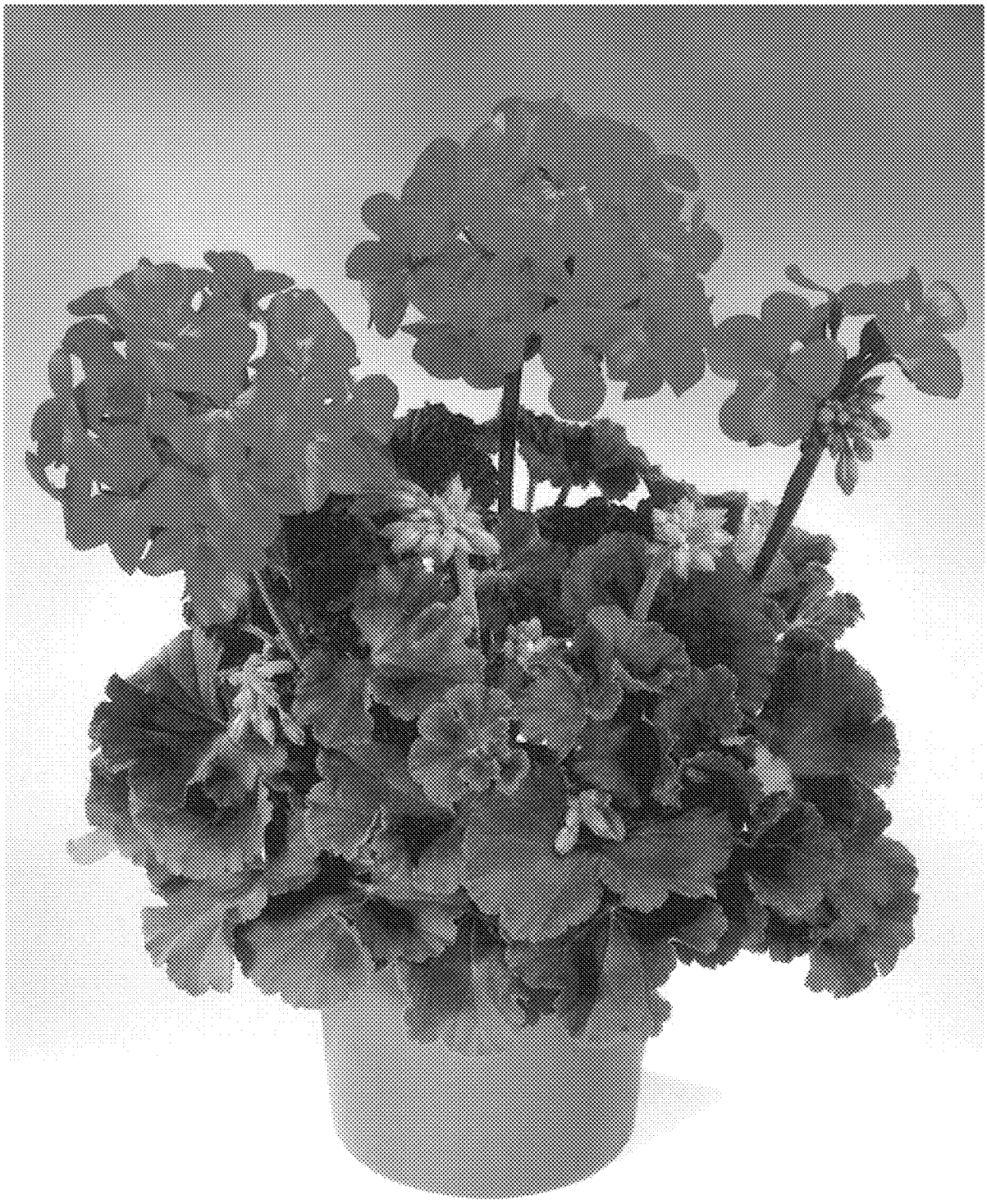

* * * * *